US010413677B2

(12) United States Patent
Houfburg et al.

(10) Patent No.: US 10,413,677 B2
(45) Date of Patent: Sep. 17, 2019

(54) VOLUME MONITORING DEVICE

(71) Applicant: Osprey Medical, Inc., Minnetonka, MN (US)

(72) Inventors: Rodney L. Houfburg, Prior Lake, MN (US); Tuan Doan, Burnsville, MN (US)

(73) Assignee: OSPREY MEDICAL, INC., Minnetonka, MN (US)

( * ) Notice: Subject to any disclaimer, the term of this patent is extended or adjusted under 35 U.S.C. 154(b) by 0 days.

(21) Appl. No.: 13/975,052

(22) Filed: Aug. 23, 2013

(65) Prior Publication Data

US 2014/0066860 A1 Mar. 6, 2014

Related U.S. Application Data

(63) Continuation-in-part of application No. 13/839,771, filed on Mar. 15, 2013, now Pat. No. 9,320,846.

(60) Provisional application No. 61/694,137, filed on Aug. 28, 2012.

(51) Int. Cl.
*A61M 5/315* (2006.01)

(52) U.S. Cl.
CPC .... *A61M 5/31573* (2013.01); *A61M 5/31568* (2013.01); *A61M 2205/3317* (2013.01); *A61M 2205/3334* (2013.01); *A61M 2205/3379* (2013.01)

(58) Field of Classification Search
CPC .............. A61M 5/315; A61M 5/31525; A61M 5/31565; A61M 5/31568; A61M 5/31571; A61M 5/3157; A61M 5/31528; A61M 5/31583; A61M 5/31515; A61M 2205/334; A61M 2205/3379–3396
See application file for complete search history.

(56) References Cited

U.S. PATENT DOCUMENTS

| | | | |
|---|---|---|---|
| 3,469,578 A | 9/1969 | Bierman |
| 3,543,759 A | 12/1970 | McWhorter |
| 3,556,122 A | 1/1971 | Laerdal |
| 3,572,375 A | 3/1971 | Rosenberg |
| 3,626,978 A | 12/1971 | Hoekstra |
| 3,633,613 A | 1/1972 | Julow |
| 3,661,174 A | 5/1972 | Cripe |

(Continued)

FOREIGN PATENT DOCUMENTS

| | | |
|---|---|---|
| DE | 19643813 A1 | 4/1998 |
| EP | 0 523 343 A1 | 1/1993 |

(Continued)

OTHER PUBLICATIONS

Cigarroa, et al., "Dosing of Contrast Material to Prevent Nephropathy in Patients with Renal Disease", Am. Jou.r of Med., Jun. 1989, pp. 649-652.

(Continued)

*Primary Examiner* — Bhisma Mehta
*Assistant Examiner* — Nilay J Shah

(57) ABSTRACT

An apparatus includes a syringe housing and a plunger slidably received within the syringe housing. A plunger magnet is secured to the plunger. A potentiometer housing is fixed to the syringe housing and includes a potentiometer disposed therein. A wiper magnet is also disposed within the potentiometer housing. Movement of the plunger magnet causes a corresponding movement of the wiper magnet.

18 Claims, 9 Drawing Sheets

(56) References Cited

U.S. PATENT DOCUMENTS

| | | | |
|---|---|---|---|
| 3,695,575 A * | 10/1972 | Hauser | B29C 45/53 366/76.1 |
| 3,818,929 A | 6/1974 | Braukmann | |
| 3,905,382 A | 9/1975 | Waterston | |
| 3,941,149 A | 3/1976 | Mittleman | |
| 3,985,141 A | 10/1976 | Stanley et al. | |
| 4,000,741 A | 1/1977 | Binard et al. | |
| 4,006,736 A | 2/1977 | Kranys et al. | |
| 4,030,497 A | 6/1977 | Binard et al. | |
| 4,044,793 A | 8/1977 | Krueger et al. | |
| 4,074,714 A | 2/1978 | Binard et al. | |
| 4,077,405 A | 3/1978 | Haerten et al. | |
| 4,084,606 A | 4/1978 | Mittleman | |
| 4,136,708 A | 1/1979 | Cosentino et al. | |
| 4,142,525 A | 3/1979 | Binard et al. | |
| 4,147,170 A | 4/1979 | Taylor | |
| 4,240,430 A | 12/1980 | Binard et al. | |
| 4,289,006 A | 9/1981 | Hallengren | |
| 4,318,400 A | 3/1982 | Peery et al. | |
| 4,329,985 A | 5/1982 | Bonchek | |
| 4,381,006 A | 4/1983 | Genese | |
| 4,392,847 A | 7/1983 | Whitney et al. | |
| 4,403,988 A | 9/1983 | Binard et al. | |
| 4,457,751 A | 7/1984 | Rodler | |
| 4,481,008 A | 11/1984 | Kurtz | |
| 4,501,291 A | 2/1985 | Siegrist | |
| 4,502,502 A | 3/1985 | Krug | |
| 4,550,747 A | 11/1985 | Woodworth et al. | |
| 4,602,700 A | 7/1986 | Szabo | |
| 4,655,746 A | 4/1987 | Daniels et al. | |
| 4,671,786 A | 6/1987 | Krug | |
| 4,744,786 A | 5/1988 | Hooven | |
| 4,755,172 A | 7/1988 | Baldwin | |
| 4,758,223 A | 7/1988 | Rydell | |
| 4,795,431 A | 1/1989 | Walling | |
| 4,813,937 A | 3/1989 | Vaillancourt | |
| 4,838,857 A * | 6/1989 | Strowe et al. | 604/67 |
| 4,845,493 A | 7/1989 | Howard | |
| 4,867,743 A | 9/1989 | Vaillancourt | |
| 4,997,420 A | 3/1991 | LeFevre | |
| 5,059,174 A | 10/1991 | Vaillancourt | |
| 5,094,148 A * | 3/1992 | Haber | A61M 5/31515 403/348 |
| 5,139,484 A * | 8/1992 | Hazon | A61M 5/1456 128/DIG. 1 |
| 5,167,631 A | 12/1992 | Thompson et al. | |
| 5,273,187 A | 11/1993 | Suzuki | |
| 5,376,785 A | 12/1994 | Chin et al. | |
| 5,460,609 A | 10/1995 | O'Donnell | |
| 5,534,691 A | 7/1996 | Holdaway et al. | |
| 5,556,386 A | 9/1996 | Todd | |
| 5,573,515 A | 11/1996 | Wilson et al. | |
| 5,575,767 A | 11/1996 | Stevens | |
| 5,662,612 A | 9/1997 | Niehoff | |
| 5,681,285 A | 10/1997 | Ford | |
| 5,685,851 A | 11/1997 | Murphy et al. | |
| 5,707,356 A | 1/1998 | Paul | |
| 5,752,940 A | 5/1998 | Grimard | |
| 5,785,681 A | 7/1998 | Indravudh | |
| 5,792,117 A | 8/1998 | Brown | |
| 5,799,700 A | 9/1998 | Teh et al. | |
| 5,800,397 A | 9/1998 | Wilson et al. | |
| 5,806,519 A | 9/1998 | Evans, III et al. | |
| 5,827,941 A | 10/1998 | Good et al. | |
| 5,840,026 A | 11/1998 | Uber, III et al. | |
| 5,840,071 A | 11/1998 | Kriesel et al. | |
| 5,882,338 A | 3/1999 | Gray | |
| 5,882,343 A | 3/1999 | Wilson et al. | |
| 5,885,216 A | 3/1999 | Evans, III et al. | |
| 5,916,165 A | 6/1999 | Duchon et al. | |
| 5,954,700 A * | 9/1999 | Kovelman | A61M 5/31525 604/189 |
| 6,019,747 A | 2/2000 | McPhee | |
| 6,086,559 A | 7/2000 | Enk | |
| 6,113,578 A | 9/2000 | Brown | |
| 6,159,180 A | 12/2000 | Kriesel et al. | |
| 6,317,623 B1 | 11/2001 | Griffiths et al. | |
| 6,397,098 B1 | 5/2002 | Uber, III et al. | |
| 6,409,699 B1 | 6/2002 | Ash | |
| 6,442,418 B1 | 8/2002 | Evans, III et al. | |
| 6,558,125 B1 | 5/2003 | Futterknecht | |
| 6,850,792 B2 | 2/2005 | Ohishi | |
| 6,858,020 B2 | 2/2005 | Rusnak | |
| 6,866,654 B2 | 3/2005 | Callan et al. | |
| 6,889,074 B2 | 5/2005 | Uber, III et al. | |
| 6,901,283 B2 | 5/2005 | Evans, III et al. | |
| 6,966,893 B2 | 11/2005 | Holtby et al. | |
| 6,969,353 B2 | 11/2005 | Brock-Fisher et al. | |
| 6,970,735 B2 | 11/2005 | Uber, III et al. | |
| 7,022,107 B1 | 4/2006 | Christensen et al. | |
| 7,065,395 B2 | 6/2006 | Lienard et al. | |
| 7,094,216 B2 | 8/2006 | Trombley, III et al. | |
| 7,255,684 B2 | 8/2007 | Zubry | |
| 7,270,648 B2 | 9/2007 | Kazemzadeh | |
| 7,326,186 B2 | 2/2008 | Trombley, III et al. | |
| 7,470,253 B2 | 12/2008 | Kriesel et al. | |
| 7,516,760 B2 | 4/2009 | Weber | |
| 7,611,503 B2 | 11/2009 | Spohn et al. | |
| 7,618,412 B2 | 11/2009 | Chernack | |
| 7,678,070 B2 | 3/2010 | Kumar et al. | |
| 7,766,885 B2 | 8/2010 | Olsen | |
| 7,815,604 B2 | 10/2010 | Massengale et al. | |
| 7,854,726 B2 | 12/2010 | Fago et al. | |
| 7,925,330 B2 | 4/2011 | Kalafut et al. | |
| 7,927,305 B2 | 4/2011 | Yribarren et al. | |
| 7,951,129 B2 | 5/2011 | Chinchoy | |
| 7,955,301 B1 | 6/2011 | McKay | |
| 8,075,490 B2 | 12/2011 | Lofgren et al. | |
| 8,147,448 B2 | 4/2012 | Sundar et al. | |
| 8,172,790 B2 | 5/2012 | Hunter et al. | |
| 8,197,443 B2 | 6/2012 | Sunder et al. | |
| 8,197,444 B1 | 6/2012 | Bazargan et al. | |
| 8,208,994 B2 | 6/2012 | Niethammer | |
| 8,257,310 B2 | 9/2012 | Donovan et al. | |
| 8,295,914 B2 | 10/2012 | Kalafut et al. | |
| 8,303,547 B2 | 11/2012 | Brown | |
| 8,323,267 B2 | 12/2012 | Haase | |
| 8,328,758 B2 | 12/2012 | Childers et al. | |
| 2001/0039396 A1 | 11/2001 | Kriesel et al. | |
| 2002/0087125 A1 | 7/2002 | Pokorney | |
| 2002/0128611 A1 | 9/2002 | Kandalaft | |
| 2003/0055380 A1 | 3/2003 | Flaherty | |
| 2003/0233069 A1 | 12/2003 | Gillespie, Jr. et al. | |
| 2004/0135078 A1 | 7/2004 | Mandro et al. | |
| 2004/0138615 A1 | 7/2004 | Lombardi | |
| 2004/0143212 A1 | 7/2004 | Trombley et al. | |
| 2004/0178255 A1 | 9/2004 | Eich et al. | |
| 2004/0226183 A1 | 11/2004 | Sielemann | |
| 2005/0020983 A1 | 1/2005 | Schreijag et al. | |
| 2005/0059931 A1 | 3/2005 | Garrison et al. | |
| 2005/0165364 A1 | 7/2005 | DiMatteo et al. | |
| 2005/0277912 A1 | 12/2005 | John | |
| 2006/0178632 A1 | 8/2006 | Trombley, III et al. | |
| 2007/0060820 A1* | 3/2007 | Lofgren et al. | 600/481 |
| 2007/0062250 A1 | 3/2007 | Krulevitch et al. | |
| 2007/0066939 A1 | 3/2007 | Krulevitch et al. | |
| 2007/0093752 A1* | 4/2007 | Zhao et al. | 604/131 |
| 2007/0161970 A1 | 7/2007 | Spohn et al. | |
| 2008/0004507 A1 | 1/2008 | Williams, Jr. et al. | |
| 2008/0147007 A1 | 6/2008 | Freyman et al. | |
| 2008/0154187 A1 | 6/2008 | Krulevitch et al. | |
| 2008/0164970 A1* | 7/2008 | Malzahn | 338/160 |
| 2008/0287865 A1 | 11/2008 | Nielsen et al. | |
| 2008/0312536 A1 | 12/2008 | Dala-Krishna | |
| 2009/0234231 A1 | 9/2009 | Knight et al. | |
| 2010/0004571 A1* | 1/2010 | Nilsson | A61H 31/006 601/41 |
| 2010/0114064 A1 | 5/2010 | Kalafut et al. | |
| 2010/0211003 A1* | 8/2010 | Sundar | A61M 5/16813 604/67 |
| 2010/0274180 A1* | 10/2010 | Donovan et al. | 604/65 |
| 2011/0092828 A1 | 4/2011 | Spohn et al. | |
| 2012/0024987 A1 | 2/2012 | Naegele Nacken | |
| 2012/0036937 A1* | 2/2012 | Sprenger et al. | 73/744 |

(56) References Cited

U.S. PATENT DOCUMENTS

| | | |
|---|---|---|
| 2012/0041427 A1 | 2/2012 | Caffey et al. |
| 2012/0116217 A1 | 5/2012 | Lee-Sepsick et al. |
| 2012/0277661 A1 | 11/2012 | Bernard et al. |
| 2012/0277667 A1 | 11/2012 | Yodat et al. |
| 2012/0283186 A1 | 11/2012 | Adams |
| 2012/0302950 A1 | 11/2012 | Landsman et al. |
| 2012/0316460 A1 | 12/2012 | Stout |
| 2013/0261729 A1 | 10/2013 | Gillick et al. |
| 2014/0066891 A1 | 3/2014 | Burns et al. |
| 2014/0163339 A1 | 6/2014 | Goldstein et al. |
| 2014/0288422 A1 | 9/2014 | Brady et al. |
| 2015/0202361 A1 | 7/2015 | Burns et al. |
| 2015/0202386 A1 | 7/2015 | Brady et al. |
| 2016/0213834 A1 | 7/2016 | Brady et al. |
| 2018/0318495 A1 | 11/2018 | Brady et al. |

FOREIGN PATENT DOCUMENTS

| | | |
|---|---|---|
| EP | 1930603 A1 | 6/2008 |
| JP | S62-184302 | 8/1987 |
| JP | H06 296690 A | 10/1994 |
| JP | H09-506288 | 6/1997 |
| JP | 2007-175444 A | 7/2007 |
| WO | WO 84/01718 A1 | 5/1984 |
| WO | WO 89/03230 A1 | 4/1989 |
| WO | WO 96/11024 A1 | 4/1996 |
| WO | WO 9817974 A1 * | 4/1998 |
| WO | 02/064196 | 8/2002 |
| WO | WO 02/098493 A1 | 12/2002 |
| WO | WO 2004/009163 A1 | 1/2004 |
| WO | WO 2005/068848 A1 | 7/2005 |
| WO | WO 2009/039203 A2 | 3/2009 |
| WO | WO 2009/065153 A2 | 5/2009 |
| WO | 2012/167720 | 12/2012 |
| WO | 2013/177135 | 11/2013 |
| WO | 2014/035647 | 3/2014 |

OTHER PUBLICATIONS

Gurm, et al., "Renal Function-Based Dosing to Define Safe Limits of Radiographic Contrast Media in Patients Undergoing Percutaneous Coronary Interventions", JACC, 2011:58:907-14.

"Evidence of a Dominant Backward-Propagating 'Suction' Wave Responsible for Diastolic Coronary Filling in Humans, Attenuated in Left Ventricular Hypertrophy" (Circulation. 2006;113:1768-1778).

PCT International Search Report and Written Opinion in International Application PCT/US2013/054510, dated Dec. 4, 2013, 16 pgs.

International Search Report and Written Opinion for Application No. PCT/US2014/052319 dated Feb. 5, 2015.

PCT International Search Report and Written Opinion in International Application PCT/US2015/021294, dated Jun. 19, 2015, 13 pgs.

PCT International Search Report and Written Opinion in International Application PCT/US2016/025671, dated Jul. 26, 2016, 16 pgs.

PCT International Search Report and Written Opinion in International Application PCT/US2016/025302, dated Jul. 20, 2016, 13 pgs.

PCT International Search Report and Written Opinion in international Application PCT/US2018/040514, dated Sep. 12, 2018, 18 pgs.

Japanese Rejection in Application 2016-536484, dated Oct. 2, 2018, 6 pages.

* cited by examiner

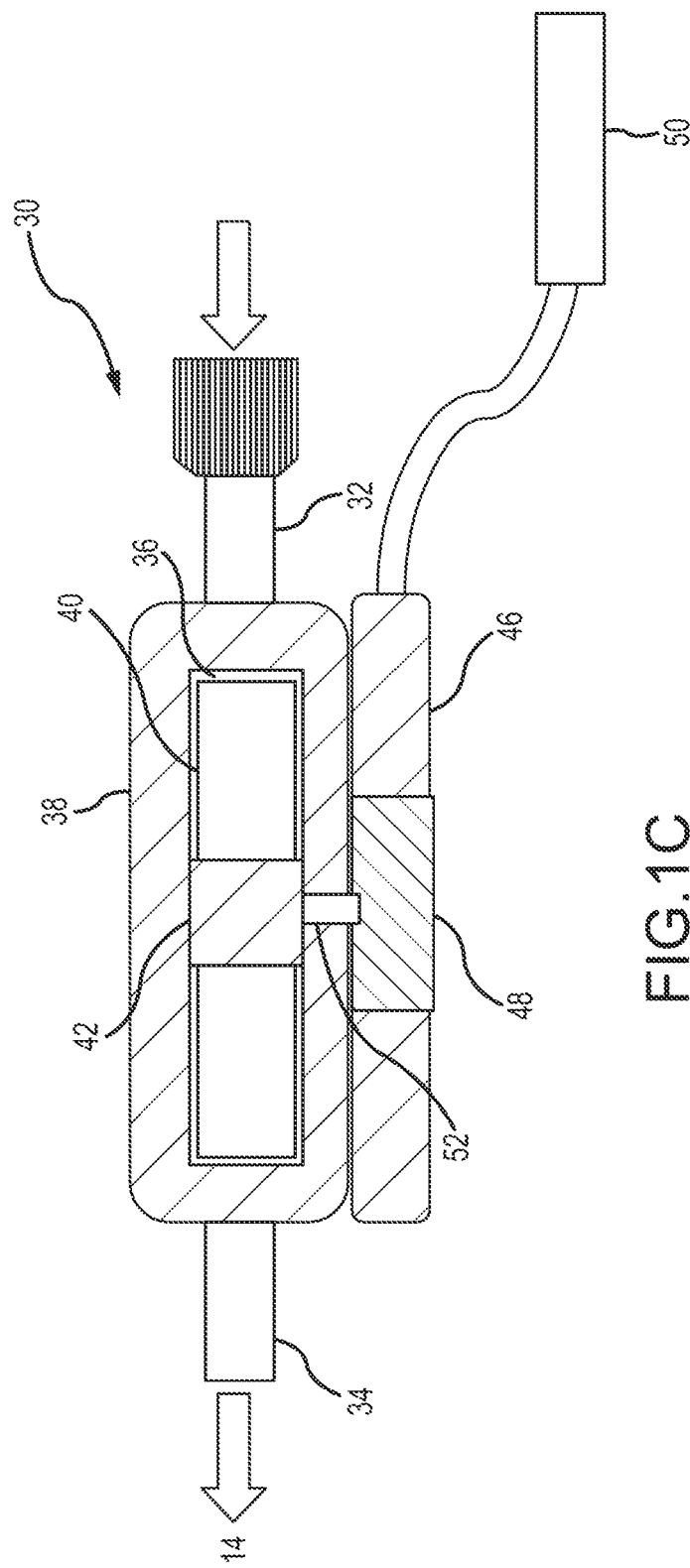

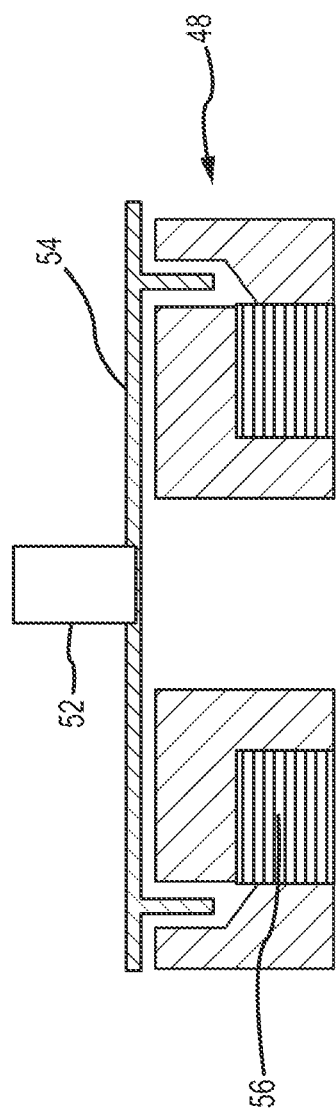

VOLUME MONITORING DEVICE

CROSS-REFERENCE TO RELATED APPLICATIONS

This application is a continuation-in-part of U.S. patent application Ser. No. 13/839,771, filed Mar. 15, 2013, entitled "Devices and Methods for Modulating Medium Delivery," to U.S. Provisional Application Ser. No. 61/694,137, filed Aug. 28, 2012, entitled "Devices and Methods for Modulating Medium Delivery," the disclosures of which are hereby incorporated by reference herein in its entirety.

INTRODUCTION

This disclosure pertains to devices and methods used to control, transform or otherwise modulate the delivery of a substance, such as radiopaque contrast, to a delivery site and/or devices and methods that may be used to measure or otherwise make quantitative assessments of a medium delivered to a delivery site. More specifically, it is the intention of the following devices and methods to modulate and/or assess the delivery of media to a vessel, vascular bed, organ, and/or other corporeal structures so as optimize the delivery of media to the intended site, while reducing inadvertent or excessive introduction of the media to other vessels, vascular beds, organs, and/or other structures, including systemic introduction.

The terms medium (media), agent, substance, material, medicament, and the like, are used generically herein to describe a variety of fluidal materials that may include, at least in part, a substance used in the performance of a diagnostic, therapeutic or/and prophylactic medical procedure and such use is not intended to be limiting.

SUMMARY

This summary is provided to introduce a selection of concepts in a simplified form that are further described below in the Detailed Description. This summary is not intended to identify key features or essential features of the claimed subject matter, is not intended to describe each disclosed embodiment or every implementation of the claimed subject matter, and is not intended to be used as an aid in determining the scope of the claimed subject matter. Many other novel advantages, features, and relationships will become apparent as this description proceeds. The figures and the description that follow more particularly exemplify illustrative embodiments.

In one aspect, the technology relates to an apparatus including: a syringe housing; a plunger slidably received within the syringe housing; a plunger magnet secured to the plunger; a potentiometer housing fixed to the syringe housing; a potentiometer disposed within the potentiometer housing; and a wiper magnet slidably received within the potentiometer housing, wherein a movement of the plunger magnet causes a corresponding movement of the wiper magnet. In an embodiment, the apparatus includes a plurality of leads extending from the potentiometer. In another embodiment, the apparatus includes an interface for connecting the plurality of leads to a measuring device, and wherein the measuring device displays a total volume injected and emits a warning of a critical outcome. In yet another embodiment, the potentiometer housing is releasably fixed to the syringe housing. In still another embodiment, the apparatus includes means for releasably securing the potentiometer housing to the syringe housing. In another embodiment of the above aspect, the means includes at least one of a clamp, a clasp, a hook and loop fastener, and a magnet. In another embodiment, the means for releasably securing the potentiometer is secured to the potentiometer housing. In another embodiment, the means for releasably securing is releasably secured to the potentiometer housing. In another aspect, the technology relates to an apparatus including: a syringe housing; a plunger slidably received within the syringe housing; a potentiometer secured to the syringe housing; a first magnet movably positionable relative to the potentiometer; and a second magnet, wherein the first magnet and the second magnet are adapted to move in tandem. In an embodiment, the apparatus includes a lead for sending an output signal from the potentiometer to an interface, wherein the interface displays a total volume injected and emits a warning of a critical outcome. In another embodiment, the output signal varies based on a position of the first magnet relative to the potentiometer. In yet another embodiment, the first magnet is disposed proximate the potentiometer. In still another embodiment, the second magnet is fixed to the plunger. In another embodiment, the second magnet includes a plurality of magnets In another aspect, the technology relates to an apparatus including: a syringe housing; a potentiometer secured to the syringe housing; a first magnet movably positionable relative to the potentiometer; and a plunger slidably received within the syringe housing, wherein the first magnet is movable based at least in part on a movement of the plunger. In an embodiment, the apparatus a second magnet secured to the plunger and aligned with the first magnet. In another embodiment, the apparatus includes a third magnet secured to the plunger and aligned with the first magnet. In yet another embodiment, the first magnet is disposed within a magnetic field formed by at least one of the second magnet and the third magnet. In still another embodiment, the apparatus includes a potentiometer housing, wherein the potentiometer and the first magnet are disposed within the potentiometer housing. In another embodiment, the apparatus includes a lead for sending an output signal from the potentiometer to an interface, wherein the interface displays a total volume injected and emits a warning of a critical outcome.

BRIEF DESCRIPTION OF THE DRAWINGS

There are shown in the drawings, embodiments which are presently preferred, it being understood, however, that the technology is not limited to the precise arrangements and instrumentalities shown.

FIG. 1C depicts an exemplary synchronized agent delivery with indirect modulation (side view), adjacent a proximal portion of such a treatment system.

FIG. 1D depicts, in side sectional view, the brake mechanism of the exemplary synchronized agent delivery arrangement of FIG. 1C.

DETAILED DESCRIPTION

Figure 1A:
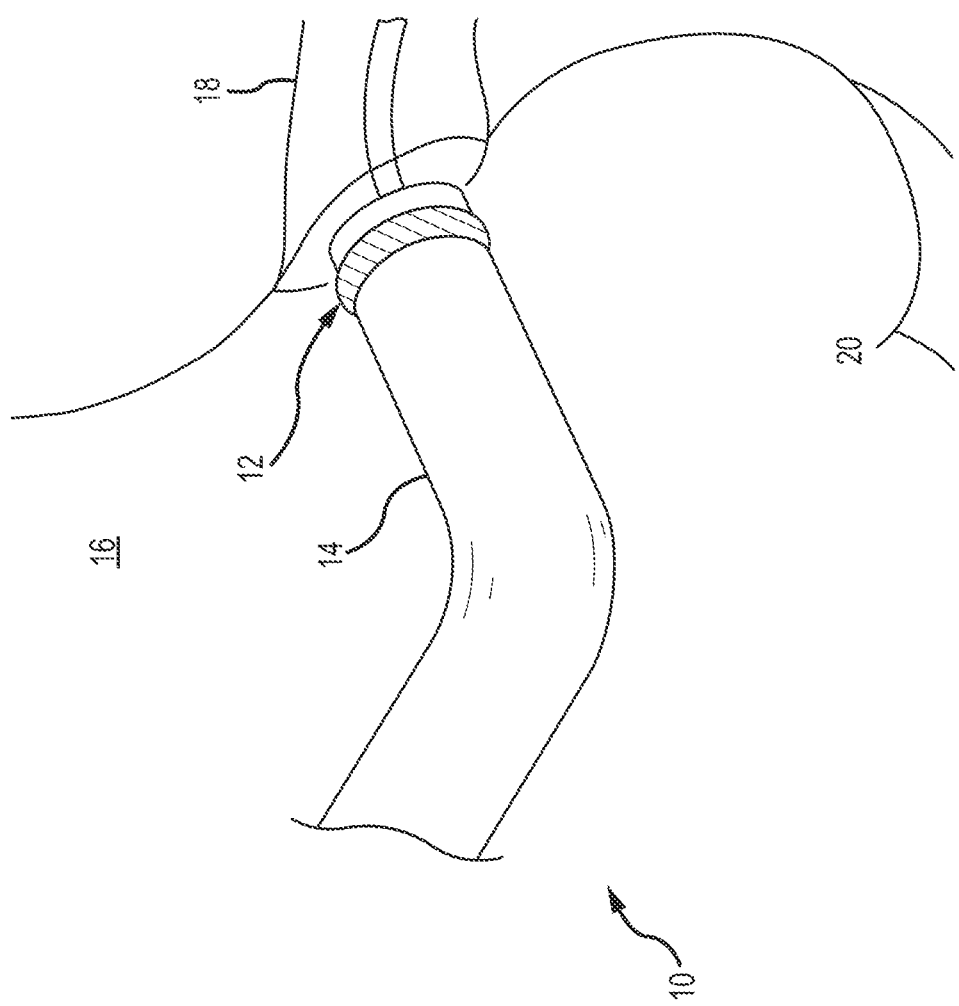
FIG. 1A depicts an exemplary synchronized agent delivery with indirect modulation, adjacent a distal portion of a treatment system therefor.

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease. The description, as well as the devices and methods described herein, may be used in modulating contrast media and/or monitoring the delivery to the coronary vasculature in prevention of toxic systemic effects of such an agent. One skilled in the art, however, would recognize that there are many other applications wherein the controlled delivery and/or quantitative assessment of a media to a specific vessel, structure, organ or site of the body may also benefit from the devices and methods disclosed herein. For simplicity, these devices and methods may be described as they relate to contrast media delivery modulation and/or measurement. As such, they may be used in the prevention of Contrast Induced Nephropathy; however, it is not intended, nor should it be construed, so as to limit the use to this sole purpose. Exemplary other uses may include the delivery, injection, modulation, or measurement of: cancer treatment agent to a tumor, thrombolytic to an occluded artery, occluding or sclerosing agent to a vascular malformation or diseased tissue; genetic agent to a muscular bed, neural cavity or organ, emulsion to the eye, bulking agent to musculature and/or sphincter, imaging agent to the lymphatic system, antibiotics to an infected tissue, supplements in the dialysis of the kidney, to name but a few.

Example—Prevention of Contrast Induced Nephropathy

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poorly or nonfunctioning kidneys may suffer from rapidly declining health, poor quality of life, and significantly shortened life expectancy. Potential consequences of CIN include: irreversible damage to the kidneys, longer hospital stays, increased risk of heart disease, increased risk of long-term dialysis, and ultimately, a higher mortality risk. For patients who acquire CIN, their risk of dying remains higher than others without CIN, and this risk can continue up to five years after their procedure. CIN has a significant economic burden on the healthcare system and currently there is no treatment available to reverse damage to the kidneys or improper kidney performance, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (of a chemical or molecular nature) of the dyes, reduce the total amount of contrast agent injected (through injection management and/or dye concentration), and remove media through coronary vasculature isolation and blood/contrast agent collection systems, to name a few. These methods and devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature). Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated, powered (versus manual, syringe-injected) contrast media injection systems. Close monitoring and control of the total quantity of contrast agent injected may have a positive impact in reducing the incidence of CIN. However, these injection systems are expensive (including capital equipment and disposables), cumbersome to use within a cath lab, and take additional time and expertise to set up and operate properly. Improper use could negate any benefits seen by better management of the quantity of the contrast agent delivered to a patient, and the additional time required to set up such a system may also add significant complexity to a procedure. The devices and methods described herein may measure or otherwise quantitatively assess the amount of medium injected or delivered to a delivery site using a relatively fast, simple, economical, and safe system.

The measurement systems described herein may be employed as a system of quantitative assessment or in combination with a modulator. Additional systems are described in U.S. patent application Ser. No. 13/839,771, the disclosure of which is hereby incorporated by reference herein in its entirety. FIGS. 1A-1D depict embodiments where a modulator is constructed so as to measure the amount of an agent delivered from the system. Conversely, FIG. 2, for example, describes the use of a measurement system for the quantitative assessment of the volume of medium delivered and the inherent analysis of the total volume delivered versus some predetermined critical amount, such as the Gurm ratio, whether or not it is used with a modulator.

It should be understood that measurements may be performed prior to a medium being modulated, simultaneously with modulation, or after the modulation process, if desired. Further, it is also contemplated that the measurement devices and methods may be used with any of the modulation systems, such as described in U.S. patent application Ser. No. 13/839,771. Moreover, the embodiments described herein are exemplary in nature and should not be construed as limiting the various combinations possible.

Some embodiments of control and modulation devices disclosed herein may send and/or receive a sensor signal so as to coordinate a valving, controlling, or otherwise modulating function on an injection agent before the agent enters an intended target injection site. Modulation may include, for example, valving (or otherwise modulating) an injection dispensed from an injection device. As described in U.S. patent application Ser. No. 13/839,771, indirect valving (or otherwise controlling mechanisms) may be proximally or distally positioned within, about, and/or upon the agent delivery system. An example of an indirect modulation control system 10 is depicted in FIGS. 1A-1D. In this example, a sensor 12 is deployed distally on a delivery catheter 14 (as seen in FIG. 1A) and a modulating device 30 (of FIG. 1B) is provided proximally. The sensor 12 of FIG. 1A is an exemplary pressure sensor positioned on the distal tip of the delivery catheter 14. As described previously, this is only one example of a type of sensor that may be used in obtaining a signal to synchronize the delivery of medium with the blood flow rate. Moreover, FIG. 1A illustrates the positioning of the sensor 12 upon the distal tip of the delivery catheter 14 within the aorta 16 to the left coronary artery 18, off the aortic root 20. The exemplary positioning of the sensor 12 in FIG. 1A should not be limited to that shown in order to perform the functions described herein, since there may be a multitude of sensor types (and commensurate signals) positioned at various locations on (i.e., as a function of respiration), through (i.e., as a function of imaging) and within the body (i.e., as a function of a variable proximate a target delivery site). Clearly, even the placement of a distal pressure sensor in exemplary FIG. 1A could take many forms, such as: a pressure wire alongside the catheter, a lumen within the catheter body for pressure measurement, a pressure sensor deployed within the distal tip of the catheter, and a pressure sensor deployed distally of the distal tip of the catheter and into the target vessel, to name but a few.

Figure 1B:
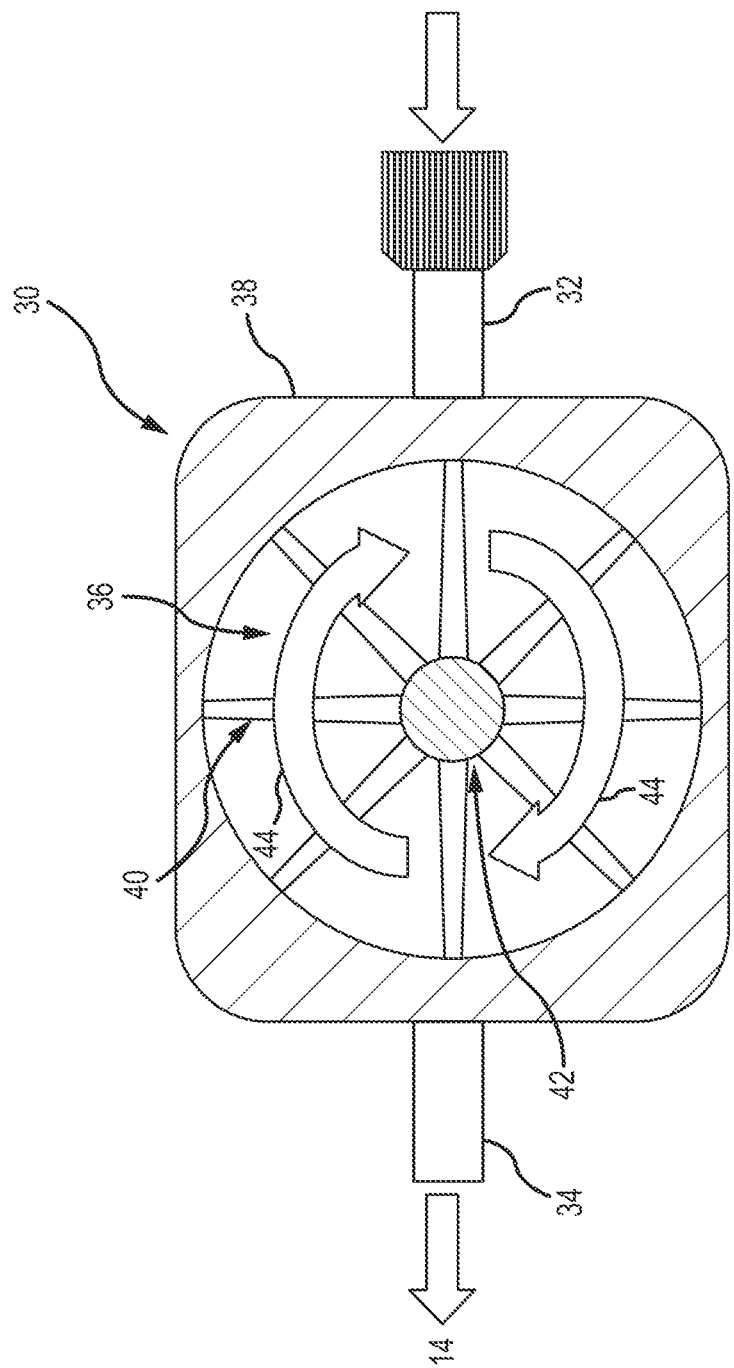
FIG. 1B depicts an exemplary synchronized agent delivery with indirect modulation (top view), adjacent a proximal portion of such a treatment system.

Referring to FIG. 1B, modulating device 30 may include an inlet port 32 (from the injection device) and an outlet port 34 (to the delivery catheter 14). The flow of injection fluid may pass through the injection port 32 and into a fluid chamber 36 within a body or housing 38 of the modulator 30. The modulator 30 may have a plurality of vane/plates 40 attached to a cylindrical hub 42 disposed within the fluid chamber 36. The vanes 40 and hub 42 may be formed to define a "pinwheel" structure of vane-hub that is capable of rotating freely (relative to fluid chamber 36 and body 38 of modulator 30) upon the injection of medium into the fluid chamber 36 through the injection port 32. The hub 42 may be designed to preferentially rotate in one direction. For example, FIG. 1B illustrates the preferential flow of fluid and rotation of the vane-hub, in a clockwise direction, via flow arrows 44. From the fluid chamber 36, injection fluid may flow out of the modulator 30 via the outlet port 34.

One advantage of the vane-hub modulator 30 depicted in FIG. 1B is that it may be easy to measure, or otherwise identify, the total volume of injection fluid delivered through the modulating device 30 (over time) since the volume of fluid passing through the device 30 during one rotation of the vane 40 or hub 42 may be easily determined, and the number of rotations simply counted by a counting mechanism. Alternatively, each "cell" of fluid between adjacent vanes 40 may be readily counted by a counting mechanism that may include a magnetic, mechanical, ultrasonic, infrared or similar measurement device capable of identifying the number of times a vane 40 and/or some other element of the device 30 has passed within its field of measurement, or by determining the number of times the axis of the hub 42 has rotated. The output of such a counting mechanism may be utilized to determine and display (in real time) the total volume of medium used during a procedure. Advantageously, in the management of medium injected, an operator or physician may readily see the amount of medium used (as determined by the counting mechanism and presented by a suitable display or indicative output). The determination of the volume (via calculations or conversions based on, for example, counted rotations) may be performed as part of the counting device, or may be performed by a display device. In addition to providing volume measurements, the counting mechanism, signal, or display may incorporate various algorithms to alert the operator before or when maximum volume of agent has been administered (based upon an operator-determined value, Maximum Acceptable Contrast Dose, Gurm ratio, etc.). For example, the Maximum Acceptable Contrast Dose index, as described by Cigarroa, et al. (June 1989) "Dosing of Contrast Material to Prevent Nephropathy in Patients with Renal Disease" Am Jour of Med. 649-652, suggests that a maximum amount of contrast injected (in mL) be equal to 5 mL×body weight (Kg)/Baseline Serum Creatinine level (in mg/dL). In another example, the maximum amount of contrast injected (in mL) as described in Gurm, et al. "Renal Function-Based Dosing to Define Safe Limits of Radiographic Contrast Media in Patients Undergoing Percutaneous Coronary Interventions" JACC 2011:58:907-14, suggests that the maximum contrast used (in mL) should be less than, or equal to, 2 if it is divided by a calculated Creatinine Clearance (mL/min) of the patient. Regardless of the indicator utilized, the system may include a display that not only provides total volume used, but also warns the operator of use as compared to one or more indicators of a maximum administration.

Continuing with the description of the exemplary modulation device 30 shown in FIGS. 1B-1C, the vane-hub modulator 30 may include two components. The first, the body 38 (described above) may be situated adjacent a controller/actuator 46 and may include the input port 32, the output port 34 and the fluid chamber 36 with rotating vane 40 and hub 42. The body 38 may come into contact with bodily fluids and, accordingly, may be disposable. The controller/actuator 46 may also include a brake mechanism 48, sensor signal, receiver 50, and the like may be used to clutch, brake, or otherwise inhibit the rotation of the hub 42 so as to provide resistance to rotation. The resistance induced to the rotation may be coordinated with a signal from sensor 12 of FIG. 1A, so as to modulate an injection from an injector to improve an agent fluid flow.

The braking, or clutching, of the modulator 30 of FIG. 1C may be performed through a variety of mechanisms, to include, for example, mechanical, hydromechanical, electromechanical, electromagnetic, chemomechanical, etc. FIG. 1C illustrates one such mechanism 48 for braking a shaft 52 of the hub 42, using electromagnetic force. The exemplary braking structure 48 is further detailed in FIG. 1D, wherein the longitudinal shaft 52 of the hub 42 is coupled to a hysteresis plate or disc 54 positioned within a magnetic coil 56. When electricity is applied to the magnetic coil 56, a magnetic flux is transferred to the hysteresis disc 54 (as it passes through the field) causing a magnetic "drag" on the disc 54. The drag, or braking, applied to the hysteresis disc 54 (and thus the shaft 52 of the hub 42) may be increased or decreased with increasing or decreasing voltage applied to the magnetic field to modulate the flow of medium as intended. When electrical current is removed, the connected disc 54 may rotate freely about an axis of shaft 52. Upon modulating, braking mechanism 48 of FIG. 1D may increase the drag (reduce the flow rate) of the agent as needed to improve the flow profile of the agent or fluid.

FIGS. 1A-AD describe one system to regulate the flow profile and determine the volume of injection agent through a modulator, and as such, are intended to illustrate the modulation monitoring, control, and measurement concepts disclosed herein without limitation. Therefore, this embodiment is but one example how one might use a modulator device and a measurement device to control the delivery of an agent, as well as measure the amount of agent delivered.

Other embodiments including devices and methods in quantitative assessment, or otherwise measurement, of the volume of delivery of an agent are described below. It is to be understood that these measurement devices may also be used in combination with a variety of agent modulators and the description is intended to be exemplary and not limiting.

Figure 2:
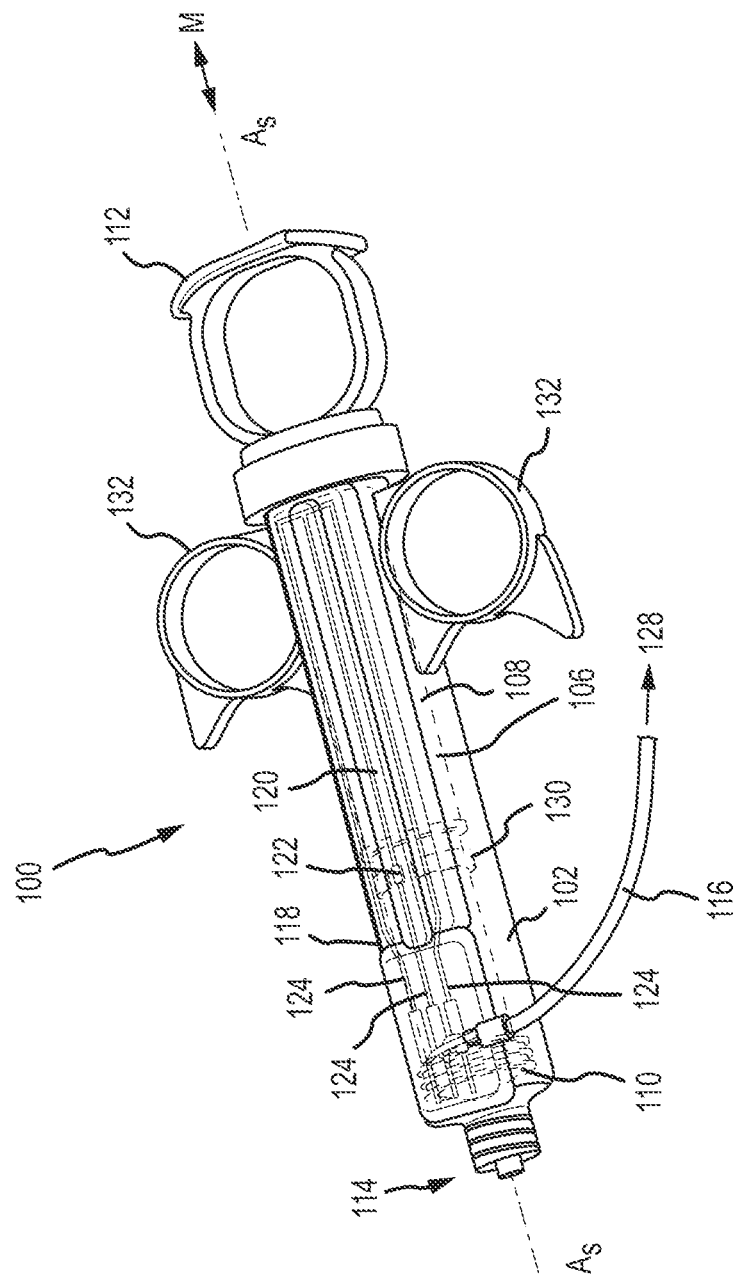
FIG. 2 depicts a perspective view of an embodiment of a monitoring syringe.
Figure 3:
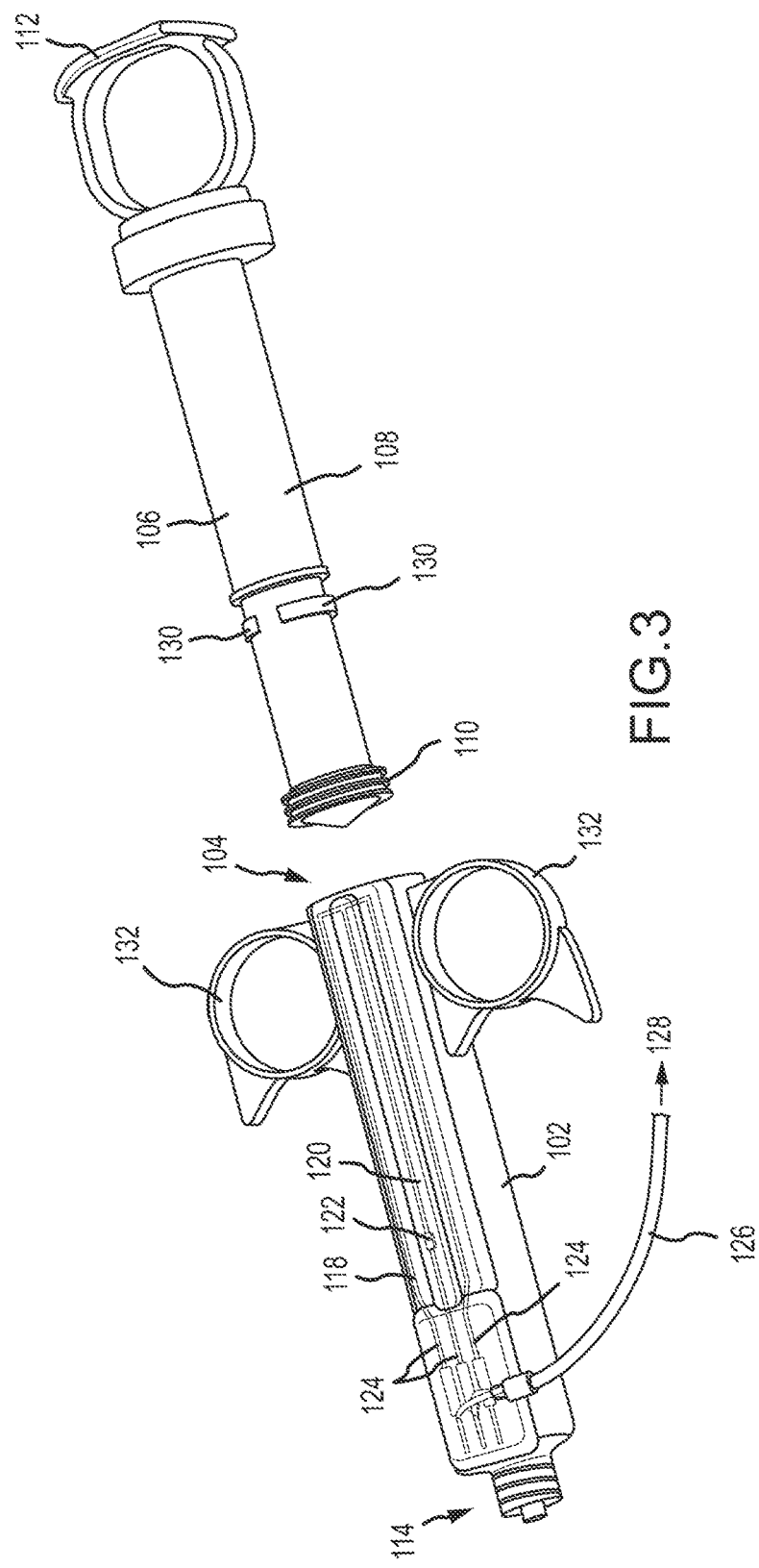
FIG. 3 depicts a partially exploded perspective view of the monitoring syringe of FIG. 2.

FIGS. 2 and 3 depict a perspective view and a perspective exploded view, respectively, of a monitoring syringe 100. The monitoring syringe 100 includes a syringe housing 102 (or chamber) defining an inner bore 104. A plunger 106 including a shaft 108 and a piston 110 is slidably received in the bore 104. More specifically, the piston 110 is slidably engaged with an interior surface of the bore 104 and linear movement M of the shaft 108 within the bore 104 moves the piston 110. Movement M is along the syringe axis $A_s$. The plunger 106 is moved back and forth within the bore 104 by the movement of a thumb-ring 112, as described in more detail below. As the plunger 106 is moved M in a direction towards the discharge end 114 of the syringe housing 102, the fluid contained therein is discharged into a tube or needle (not shown) and delivered to a patient. Note that throughout the description a cylindrical-type chamber 102 and inner bore 104 are described; however, it is contemplated that there might be a variety of constructions of a housing/bore 102/104 and plunger that provide the function as anticipated herein and the shape (including rectangular, ovular, triangular cross-section, etc.), in and of itself, should not be limiting.

In the depicted embodiment, a potentiometer housing 118 is secured to an exterior surface of the syringe housing 102. The potentiometer housing 118 encloses a linear potentiometer 120. In certain embodiments, the linear potentiometer 120 may be manufactured by various manufacturers. A wiper magnet 122 is also disposed within the potentiometer housing 118. One or more leads or wires 124 extend from an end of the potentiometer housing 118. The wires are joined within a cable 116 that connects at an end 128 to an interface unit that analyzes the output of the potentiometer 120 and provides this information to a user of the monitoring syringe 100, typically on a display. The displayed information may include volume of the chamber, volume remaining, volume dispensed, fluid type, flow rate, fluid pressure or temperature and/or other information, as required or desired for a particular application. In the depicted embodiment, a plurality of plunger magnets 130 are secured to the shaft 108 of the plunger 106. The plunger magnets 130 are "C" or arc-shaped and substantially surround the shaft 108 of the plunger 106. Movement of the plunger magnets 130 (due to movement of the plunger 106) moves the wiper magnet 122. The changing position of the wiper magnet 122 changes the electrical output of the linear potentiometer 120. These changes allow the interface to determine the various types of information listed above, based on a known diameter and length of the bore 104 of the syringe housing 102. Two finger rings 132 receive the fingers of a user during use.

The interaction between the magnetic fields produced by the wiper magnet 122 and the plunger magnets 130 has been discovered to produce extremely accurate movement of the wiper magnet 122. This accurate movement results in very accurate signals sent by the potentiometer 120 to the interface. In the depicted embodiment, the plunger magnet 130 is disposed within the syringe housing 102 (about the plunger 106) and the wiper magnet 122 is disposed within the potentiometer housing 118. Accordingly, these magnets are not in contact. It has been discovered, in various configurations, that utilizing a magnetic material and a non-magnetic material may produce less accurate results. As an example, during testing, a non-magnetic material was utilized as a wiper within the potentiometer housing 118. Magnets 130 such as the types described herein were secured to the plunger 106. It was noted that even though the magnetic field produced by the plunger magnets 130 were able to move the wiper along the potentiometer 120, the movement of the wiper could be susceptible to lagging behind the movement of the plunger magnet 130. In this configuration, if the plunger 106 was actuated at too high of a rate, friction within the potentiometer housing 118 might cause the wiper to drag to such an extent that the wiper was released from the magnetic field of the plunger magnets 130, and thus making inaccurate measurements. When magnetic material was used for both the wiper magnet 122 and the plunger magnets 130, very little lag occurred as the opposing magnetic fields were better able to sustain matching movement of the wiper magnet 122 and the plunger magnet 130.

Figure 4A:
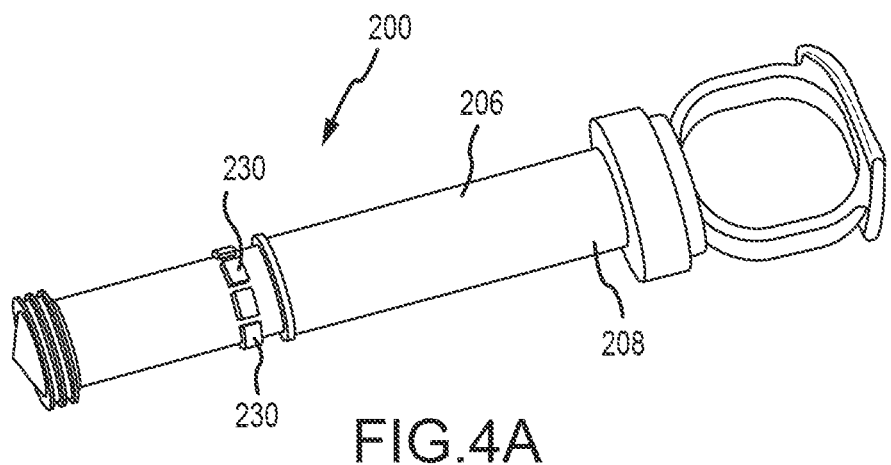
FIG. 4A depicts a partial enlarged perspective view of another embodiment of a monitoring syringe.
Figure 4B:
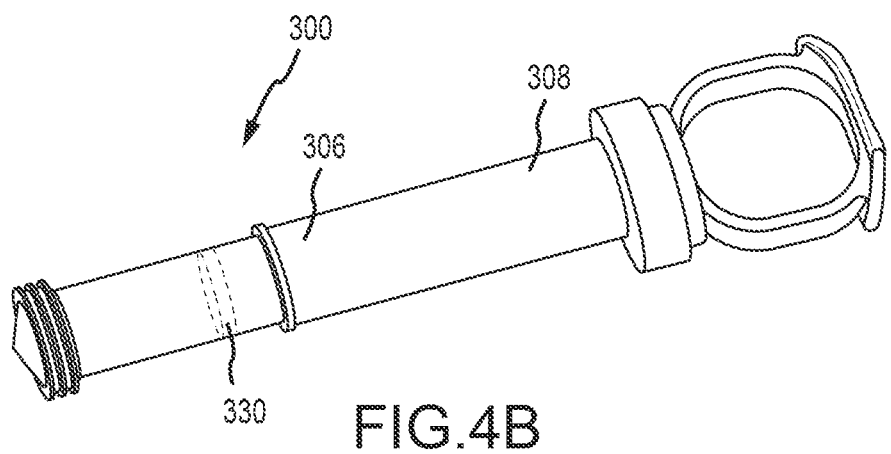
FIG. 4B depicts a partial enlarged perspective view of another embodiment of a monitoring syringe.

FIG. 4A depicts a partial enlarged perspective view of another embodiment of a monitoring syringe 200. In this embodiment, a plunger 206 includes a shaft 208. Rather than the two arc magnets depicted above in FIGS. 2 and 3, the depicted embodiment includes a plurality of substantially square plunger magnets 230 that are secured directly to the plunger shaft 208. The shape of the plunger 206 (or shaft 208) and the magnets 230 may not be critical. It is notable, however, that the magnets 130 are disposed about the outer circumference of the shaft 208. And, some portion of the plunger 206 (portion 110 as shown in FIG. 2, for example) should be in sealing, but slideable, relationship within chamber 104. FIG. 4B depicts a partial enlarged perspective view of another embodiment of a monitoring syringe 300. Here, a plunger magnet 330 is disposed within a shaft 308 of a plunger 306. The magnet 330 may be secured in place with an adhesive or may be press-fit to a hollow portion of the shaft 308. Further, it is to be understood that there may be a variety of ways to construct the plunger/shaft 206/208 to accomplish the same function. As an example, magnet sections 330 might be a separate element affixing both ends of the shaft 208 together.

Figure 5A:
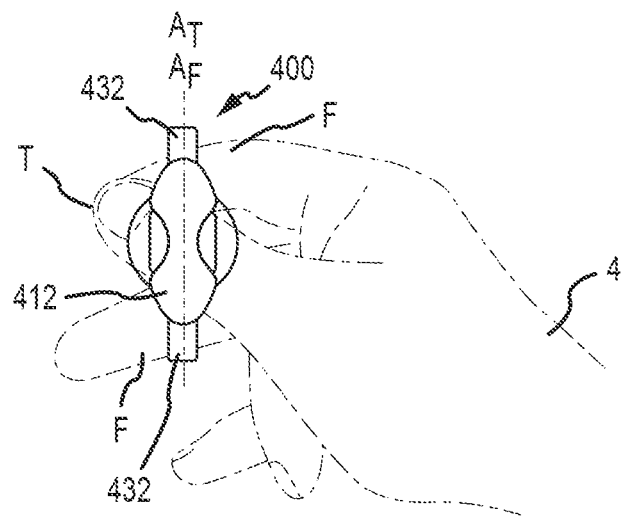
FIGS. 5A-5C depict a method of using a monitoring device.
Figure 5B:
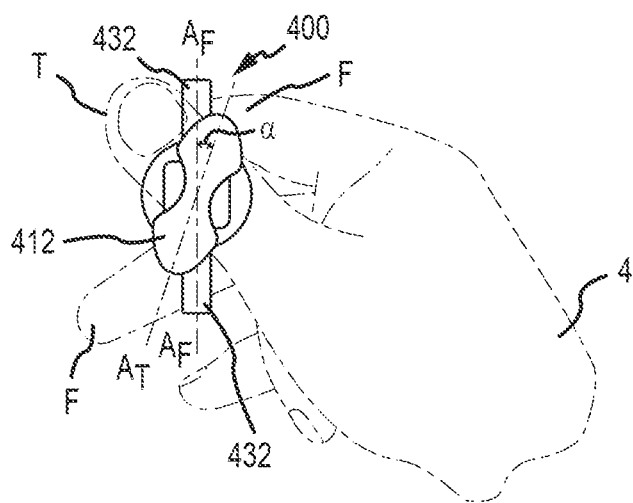
Figure 5C:
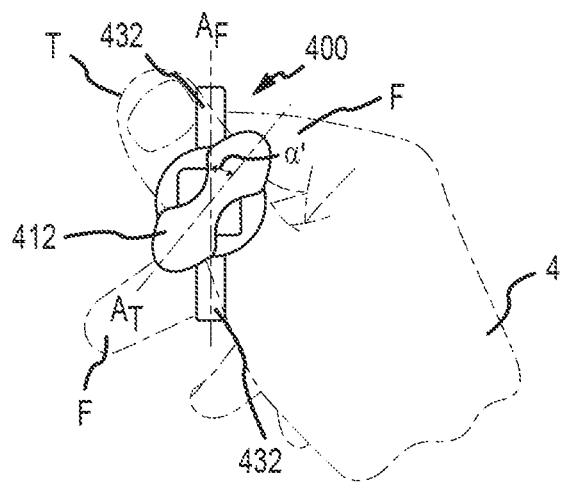

It should be noted that other orientations and positions of the plunger magnet or magnets are contemplated. In certain embodiments, the plunger magnets are oriented so as to substantially surround the shaft 108 of the plunger 106. In other embodiments, the magnet, for example, may be located within the shaft of the plunger. Regardless, the plunger magnet or magnets are oriented such that the plunger magnet remains within the magnetic field of the wiper magnet and vice versa, even during axial rotation of the plunger (that is about the syringe axis $A_s$ of FIG. 2). Without this relationship, one might receive inaccurate readings from the monitoring syringe device. If a single discrete plunger magnet is utilized, and disposed only on a small portion of the plunger, the chances of the wiper magnet passing outside of the plunger magnet magnetic field can greatly increase, especially as the plunger is rotated during use. FIGS. 5A-5C illustrate this problem.

In FIG. 5A, a user 4 holds a monitoring syringe 400 in their right hand, with the plunger in the forward-most position. The user's thumb T is located within the thumb ring 412 and first two fingers F are located within the finger rings 432. In the depicted embodiment, the syringe housing defines the syringe axis $A_S$ (depicted in FIG. 2). Other axes relevant to the present discussion are also depicted. First, a finger ring axis $A_F$ bisects the two finger rings 432 and is substantially orthogonal to the syringe axis $A_S$. Second, a thumb ring axis $A_T$, bisects a thumb ring 412, which is used to withdraw and advance the plunger. The thumb ring axis $A_T$ is also substantially orthogonal to the syringe axis A. It should be noted that the position of the finger rings 432, in this example, is fixed on the syringe housing, much like the position of the potentiometer may be fixed on the chamber housing. Accordingly, the changing angular position of the thumb ring axis $A_T$ relative to the finger ring axis $A_F$ could also be described as the changing position of the thumb ring axis $A_T$ to any element on the syringe housing.

When in the initial position of FIG. 5A, the thumb ring axis $A_T$ may be substantially parallel to the finger ring axis $A_F$. As the user's thumb T is pulled back, as depicted in FIG. 5B, the physiology of the thumb T may cause a rotation of the plunger (as indicated by the position of the thumb ring axis $A_T$). Here, an angle α (when viewed from the end of the syringe 400, as depicted) may open between the finger ring axis $A_F$ and the thumb ring axis $A_T$. A more pronounced angle α' may be produced as the thumb T is withdrawn to the final position, as depicted in FIG. 5C. Thus, orientation of the magnets about the shaft of the plunger may help ensure that the magnetic fields produced by the plunger magnet and wiper magnet remain aligned, even as the angular position of the plunger within the syringe housing changes during use. If only a single discrete plunger magnet was disposed on the outside surface of the plunger, it might be moved out of the magnetic field of the wiper magnet as the plunger rotated about the syringe axis $A_S$, as depicted by the increasing angles α, α' between the thumb ring axis $A_T$ and finger ring axis $A_F$. Similar angular movement of the thumb ring axis $A_T$ is likely as the plunger is returned to the original position. Of course, a user 4 could carefully keep the angular position of the plunger fixed within the syringe/chamber housing during use. Or one might design a device incapable of rotation. However, both options might result in lower acceptance by users, practically and/or physiologically. Another advantage to the depicted device is that it may be used by both the left and the right hands of a user, without requiring any additional configuration or modifications. Accordingly, the technologies disclosed herein include one or more plunger magnets configured to maintain the magnetic field about the wiper magnet, thus ensuring that normal rotation of the plunger during use does not adversely affect operation of device, or readings from the potentiometer.

Figure 6:
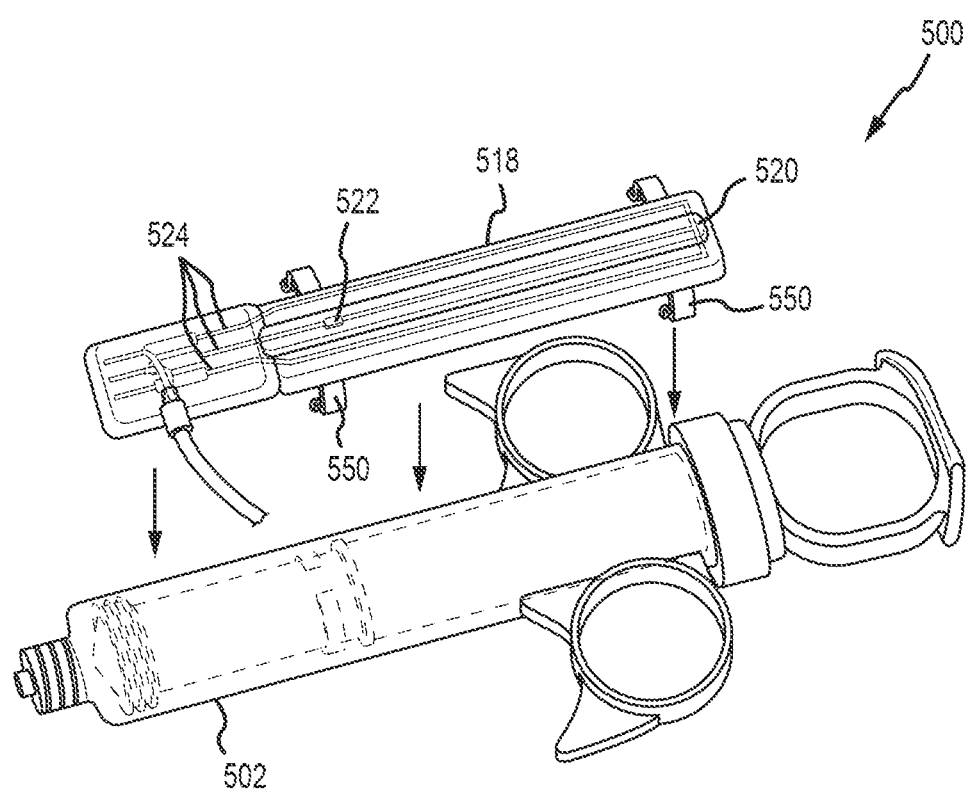
FIG. 6 depicts a partially exploded perspective view of another embodiment of a monitoring syringe.

FIG. 6 depicts another embodiment of a monitoring syringe 500. In this case, the potentiometer housing 518, containing the potentiometer 520, wiper magnet 522, and wires 524, is detachable secured to the syringe housing 502. The potentiometer housing 520 may be secured with clips, C-clamps, resilient catches, or other elements (such as 550) that allow the potentiometer housing 520 to be removed from the syringe housing 502. Such a configuration may be desirable so the potentiometer housing 518 and related components may be reused on a different syringe, typically after a medical procedure. The potentiometer housing 518 may be removed from a first syringe housing 502 and reattached to a second syringe housing at a later time. Once the wires 524 are reconnected to the interface (as described above) a calibration program may be executed so as to calibrate the potentiometer 520 for the new syringe.

The monitoring systems described herein may be utilized to deliver any types of fluids to a patient during a medical procedure. Such fluids may include medium (media), agents, substances, materials, medicaments, and the like. It should be noted that these terms are used generically herein to describe a variety of fluidal materials that may include, at least in part, a substance used in the performance of a diagnostic, therapeutic or/and prophylactic medical procedure and such use is not intended to be limiting. It should be understood that the medium delivery modulation and/or measurement devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

What is claimed is:

1. A medical syringe apparatus comprising:
   a medical syringe housing;
   a plunger comprising an axis, wherein the plunger is slidably received within the medical syringe housing so as to move along the axis;
   a plurality of plunger magnets secured to and radially disposed on the plunger at a single location along the axis, said single location being substantially surrounded circumferentially by the plurality of plunger magnets;
   a potentiometer housing fixed to the medical syringe housing;
   a potentiometer disposed within the potentiometer housing; and
   a wiper magnet slidably received within the potentiometer housing, wherein a movement of the plurality of plunger magnets causes a corresponding movement of the wiper magnet.

2. The apparatus of claim 1, further comprising a plurality of leads extending from the potentiometer.

3. The apparatus of claim 2, further comprising an interface for connecting the plurality of leads to a measuring device, and wherein the measuring device displays a total volume injected and emits a warning of a critical outcome.

4. The apparatus of claim 1, wherein the potentiometer housing is releasably fixed to the medical syringe housing.

5. The apparatus of claim 4, further comprising a securement element for releasably securing the potentiometer housing to the medical syringe housing.

6. The apparatus of claim 5, wherein the securement element comprises at least one of a clamp, a clasp, a hook and loop fastener, and a magnet.

7. The apparatus of claim 5, wherein the securement element for releasably securing the potentiometer is connected to the potentiometer housing.

8. The apparatus of claim 5, wherein the securement element for releasably securing the potentiometer is releasably connected to the potentiometer housing.

9. A medical syringe apparatus comprising:
   a medical syringe housing;

a medical plunger slidably received within and rotatably received within the medical syringe housing;

a potentiometer secured to and along a body of the medical syringe housing, said potentiometer being disposed within a potentiometer housing;

a first magnet movably positionable in the potentiometer housing, wherein the first magnet is movable relative to the potentiometer; and a second magnet secured to and disposed on the medical plunger, wherein the first magnet and the second magnet are adapted to move linearly in tandem during a movement of the medical plunger, wherein the movement of the medical plunger is both rotational and linear.

10. The apparatus of claim 9, further comprising a lead for sending an output signal from the potentiometer to an interface, wherein the interface displays a total volume injected and emits a warning of a critical outcome.

11. The apparatus of claim 10, wherein the output signal varies based on a position of the first magnet relative to the potentiometer.

12. The apparatus of claim 9, wherein the first magnet is disposed proximate the potentiometer.

13. The apparatus of claim 12, wherein the second magnet comprises a plurality of magnets.

14. A medical syringe apparatus comprising:

a medical syringe housing;

a potentiometer secured to and along a body of the medical syringe housing, said potentiometer being disposed within a potentiometer housing;

a first magnet disposed within the potentiometer housing and linearly movably positionable relative to the potentiometer; and a medical plunger linearly slidably received and rotatably received within the medical syringe housing, wherein the first magnet is linearly movable based at least in part on a linear movement of the medical plunger, regardless of an angle of rotation of the medical plunger.

15. The apparatus of claim 14, further comprising a second magnet secured to the medical plunger and aligned with the first magnet.

16. The apparatus of claim 15, further comprising a third magnet secured to the medical plunger and aligned with the first magnet.

17. The apparatus of claim 16, wherein the first magnet is disposed within a magnetic field formed by at least one of the second magnet and the third magnet.

18. The apparatus of claim 14, further comprising a lead for sending an output signal from the potentiometer to an interface, wherein the interface displays a total volume injected and emits a warning of a critical outcome.

* * * * *